United States Patent [19]

Gehring et al.

[11] Patent Number: 4,810,283
[45] Date of Patent: Mar. 7, 1989

[54] NOVEL 1-ARYL-4-NITRO-PYRAZOLE HERBICIDES AND PLANT GROWTH REGULATORS, COMPOSITIONS AND USE

[75] Inventors: Reinhold Gehring, Wuppertal; Otto Schallner, Monheim; Jörg Stetter, Wuppertal; Hans-Joachim Santel, Leverkusen; Robert R. Schmidt; Klaus Lürssen, both of Bergisch-Gladbach, all of Fed. Rep. of Germany

[73] Assignee: Bayer Aktiengesellschaft, Leverkusen, Fed. Rep. of Germany

[21] Appl. No.: 925,639

[22] Filed: Oct. 30, 1986

[30] Foreign Application Priority Data

Oct. 31, 1985 [DE] Fed. Rep. of Germany ....... 3538731

[51] Int. Cl.⁴ ................... A01N 43/56; C07D 231/16
[52] U.S. Cl. ............................................ 71/92; 71/74; 71/76; 514/404; 514/407; 540/603; 544/131; 544/140; 546/193; 546/211; 546/279; 548/362; 548/374; 548/376
[58] Field of Search .................. 546/279, 193, 211; 548/362, 376, 374; 544/131; 540/603; 71/92, 74, 76

[56] References Cited

FOREIGN PATENT DOCUMENTS 0154115 9/1985 European Pat. Off. .
3226513 2/1983 Fed. Rep. of Germany .
3402308 8/1985 Fed. Rep. of Germany .

Primary Examiner—Robert W. Ramsuer
Attorney, Agent, or Firm—Sprung Horn Kramer & Woods

[57] ABSTRACT

Novel 1-aryl-4-nitro-pyrazoles which exhibit herbicidal and plant growth-regulating activity of the formula

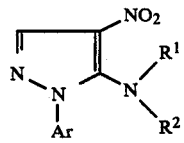

in which
$R^1$ represents in each case optionally substituted alkyl, alkenyl, alkinyl or cycloalkyl and
$R^2$ represents hydrogen, or represents in each case optionally substituted alkyl, alkenyl, alkinyl or cycloalkyl, or represents a radical

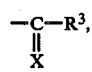

or
$R^1$ and $R^2$, together with the nitrogen atom to which they are bonded, represent a saturated heterocyclic radical, which can optionally contain further hetero atoms, and
Ar represents in each case optionally substituted phenyl or pyridyl,
wherein
X represents oxygen or sulphur and
$R^3$ represents hydrogen, alkyl, alkoxy, alkoxy-alkyl, alkylthio, alkylthioalkyl, alkylamino, di-alkylamino, halogenoalkyl, alkenyl or alkinyl, or represents optionally substituted cycloalkyl, or represents optionally substituted aryl, or represents optionally substituted aryloxy, or represents optionally substituted arylthio, or represents optionally substituted arylamino,
but wherein $R^2$ only represents hydrogen or a radical

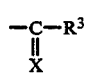

if $R^1$ does not simultaneously represent unsubstituted alkyl or represent alkyl which is substituted by an alkoximino radical.

14 Claims, No Drawings

NOVEL 1-ARYL-4-NITRO-PYRAZOLE HERBICIDES AND PLANT GROWTH REGULATORS, COMPOSITIONS AND USE

The invention relates to new 1-aryl-4-nitropyrazoles, several processes for their preparation and their use as herbicides and plant growth regulators. It is already known that certain substituted 5-amino-1-phenyl-pyrazoles, such as, for example, 4-cyano-5-propionamido-1-(2,4,6-trichlorophenyl)-pyrazole, have herbicidal properties (compare, for example, DE-OS (German Published Specification) No. 3,226,513).

However, the herbicidal action of these known compounds against weeds, like their tolerance towards important crop plants, is not always completely satisfactory in all fields of use.

Nothing is known of a plant growth regulatory activity of the known compounds.

New 1-aryl-4-nitro-pyrazoles of the general formula (I)

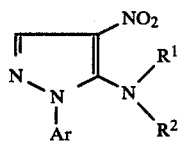

in which
$R^1$ represents in each case optionally substituted alkyl, alkenyl, alkinyl or cycloalkyl and
$R^2$ represents hydrogen, or represents in each case optionally substituted alkyl, alkenyl, alkinyl or cycloalkyl, or represents a radical

or
$R^1$ and $R^2$, together with the nitrogen atom to which they are bonded, represent a saturated heterocyclic radical, which can optionally contain further hetero atoms, and
Ar represents in each case optionally substituted phenyl or pyridyl,
wherein
X represents oxygen or sulphur and
$R^3$ represents hydrogen, alkyl, alkoxy, alkoxyalkyl, alkylthio, alkylthioalkyl, alkylamino, dialkylamino, halogenoalkyl, alkenyl or alkinyl, or represents optionally substituted cycloalkyl, or represents optionally substituted aryl, or represents optionally substituted aryloxy, or represents optionally substituted arylthio, or represents optionally substituted arylamino,
but wherein $R^2$ only represents hydrogen or represents a radical

if $R^1$ does not simultaneously represent unsubstituted alkyl or represent alkyl which is substituted by an alkoximino radical, have been found.

It has furthermore been found that the new 1-aryl-4-nitro-pyrazoles of the formula (I)

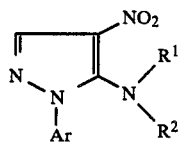

in which
$R^1$ represents in each case optionally substituted alkyl, alkenyl, alkinyl or cycloalkyl and
$R^2$ represents hydrogen, or represents in each case optionally substituted alkyl, alkenyl, alkinyl or cycloalkyl, or represents a radical

or
$R^1$ and $R^2$, together with the nitrogen atom to which they are bonded, represent a saturated heterocyclic radical, which can optionally contain further hetero atoms, and
Ar represents in each case optionally substituted phenyl or pyridyl,
wherein
X represents oxygen or sulphur and
$R^3$ represents hydrogen, alkyl, alkoxy, alkoxyalkyl, alkylthio, alkylthioalkyl, alkylamino, dialkylamino, halogenoalkyl, alkenyl or alkinyl, or represents optionally substituted cycloalkyl, or represents optionally substituted aryl, or represents optionally substituted aryloxy, or represents optionally substituted arylthio, or represents optionally substituted arylamino,
but wherein $R^2$ only represents hydrogen or represents a radical

if $R^1$ does not simultaneously represent unsubstituted alkyl or represent alkyl which is substituted by an alkoximino radical, are obtained with the aid of the processes described below:

1-Aryl-4-nitro-pyrazoles of the formula (I)

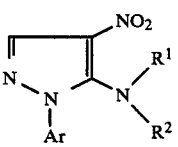

in which $R^1$, $R^2$ and Ar have the abovementioned meaning, are obtained by a process in which (a) 5-halogeno-4-nitro-1-aryl-pyrazoles of the formula (II)

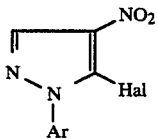  (II)

in which
Ar has the abovementioned meaning and
Hal represents halogen,
are reacted with amino compounds of the formula (III)

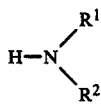  (III)

in which $R^1$ and $R^2$ have the abovementioned meaning, if appropriate in the presence of a diluent and if appropriate in the presence of an acid-binding agent, or in which (b) 5-amino-4-nitro-1-aryl-pyrazoles of the formula (Ia)

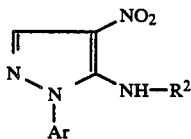  (Ia)

in which $R^2$ and Ar have the abovementioned meaning, are reacted with alkylating agents of the formula (IV)

  (IV)

in which
$R^1$ has the abovementioned meaning and
A represents an electron-withdrawing leaving group, if appropriate in the presence of a diluent, if appropriate in the presence of an acid-binding agent and if appropriate in the presence of a catalyst; or (c) 5-amino-4-nitro-1-aryl-pyrazoles of the formula (Ib)

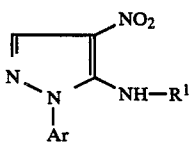  (Ib)

in which $R^1$ and Ar have the abovementioned meaning, are obtained by a process in which the 5-acylamino-4-nitro-1-aryl-pyrazoles obtainable by process (b), of the formula (Ic)

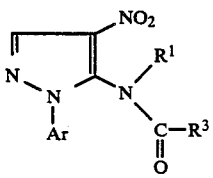  (Ic)

in which $R^1$, $R^2$ and Ar have the abovementioned meaning, are reacted with acids or bases, if appropriate in the presence of a diluent; or (d) the substituted 5-amino-4-nitro-1-arylpyrazoles of the formula (Id)

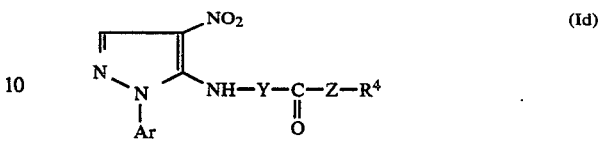  (Id)

in which
Ar has the abovementioned meaning,
Y represents a divalent alkylene, alkenylene or alkinylene radical,
Z represents oxygen or represents a radical

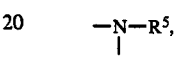

$R^4$ represents alkyl, alkenyl or alkinyl, or, in the case where Z represents an —NH— radical or an alkanesulphonamido radical, also represents hydrogen, and, in the case where Z represents oxygen, also represents one equivalent of an inorganic cation or of an optionally substituted ammonium ion, and
$R^5$ represents hydrogen, alkyl, alkenyl, alkinyl or alkoxy, or represents alkylsulphonyl, or
$R^4$ and $R^5$, together with the nitrogen atom to which they are bonded, represent a heterocyclic radical,
are obtained by a process in which the pyrazolylcarboxylic acid derivatives obtainable by process (c), of the formula (ie)

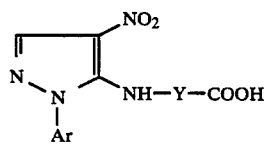  (Ie)

in which Ar and Y have the abovementioned meaning, are reacted with compounds of the formula (V)

  (V)

in which Z and $R^4$ have the abovementioned meaning, if appropriate in the presence of a diluent and if appropriate in the presence of a reaction auxiliary.

Finally, it has been found that the new 1-aryl-4-nitropyrazoles of the formula (I) have herbicidal properties, and in particular also selective herbicidal and growth regulatory properties.

Surprisingly, the 1-aryl-4-nitro-pyrazoles of the general formula (I) according to the invention exhibit a better herbicidal activity against problem weeds and simultaneously a better selectivity against important crop plants than the substituted 5-amino-1-phenylpyrazoles known from the prior art, such as, for example, 4-cyano-5-propionamido-1-(2,4,6-trichlorophenyl)-pyrazole, which are closely related compounds chemically and from the point of view of their action.

Formula (I) provides a general definition of the 1-aryl-4-nitro-pyrazoles according to the invention.

Preferred compounds of the formula (I) are those in which $R^1$ represents alkyl, alkenyl or alkinyl with in each case up to 8 carbon atoms and in each case optionally nonsubstituted or polysubstituted by identical or different substituents, possible substituents in each case being: halogen, cyano, nitro, hydroxyl, straight-chain or branched alkoxy with 1 to 6 carbon atoms, amino, in each case straight-chain or branched alkylamino or dialkylamino with in each case 1 to 6 carbon atoms in the individual alkyl parts, carboxyl and a radical

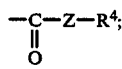

$R^1$ furthermore represents cycloalkyl which has 3 to 7 carbon atoms and is optionally monosubstituted or polysubstituted by identical or different substituents from the group comprising halogen and/or straight-chain or branched alkyl with 1 to 4 carbon atoms, $R^2$ represents hydrogen, or represents alkyl, alkenyl or alkinyl with in each case up to 8 carbon atoms and in each case optionally monosubstituted or polysubstituted by identical or different substituents, possible substituents in each case being: halogen, cyano, nitro, hydroxyl, straight-chain or branched alkoxy with 1 and 6 carbon atoms, amino and in each case straight-chain or branched alkylamino and dialkylamino with in each case 1 and 6 carbon atoms in the individual alkyl parts; $R^2$ furthermore represents cycloalkyl which has 3 and 7 carbon atoms and is optionally monosubstituted or polysubstituted by identical or different substituents from the group comprising halogen and/or straigh-chain or branched alkyl with 1 to 4 carbon atoms, or furthermore represents a radical

or $R^1$ and $R^2$, together with the nitrogen atom to which they are bonded, represent a 3- to 7-membered satuated heterocyclic radical which can contain up to 2 further hetero atoms, in particular nitrogen, oxygen and/or sulphur, and Ar presents phenyl, 2-pyridyl, 3-pyridyl or 4-pyridyl, in each case optionally monosubstituted or polysubstituted by identical or different substituents, possible substituents in each case being: cyano, nitro, halogen, in each case straight-chain or branched alkyl, alkoxy and alkoxycarbonyl with in each case 1 to 4 carbon atoms, in each case straight-chain or branched halogenoalkyl and halogenoalkoxy with in each case 1 to 4 carbon atoms and 1 to 9 identical or different halogen atoms and a radical $-S(O)_n-R^6$ wherein X represents oxygen or sulphur, $R^3$ represents hydrogen, or represents in each case straight-chain or branched alkyl, alkoxy, alkoxyalkyl, alkylthio, alkylthioalkyl, alkylamino, dialkylamino or halogenoalkyl with in each case 1 to 4 carbon atoms in the individual alkyl parts and, in the case of the halogenoalkyl, with 1 to 9 identical or different halogen atoms, or represents in each case straight-chain or branched alkenyl or alkinyl with in each case 2 to 4 carbon atoms, or furthermore represents cycloalkyl which has 3 to 7 carbon atoms and is optionally monosubstituted or polysubstituted by identical or different substituents from the group comprising halogen, alkyl and halogenoalkyl with in each case 1 to 4 carbon atoms and, in the case of the halogenoalkyl, with 1 to 5 halogen atoms, or represents phenyl, phenoxy, phenylthio or phenylamino, in each case optionally monosubstituted or polysubstituted by identical or different substituents, possible substituents on the phenyl in each case being: halogen and in each case straight-chain or branched alkyl, alkoxy and halogenoalkyl with in each case 1 to 4 carbon atoms and, in the case of the halogenoalkyl, with 1 to 9 identical or different halogen atoms, Z represents oxygen or a radical

$R^4$ represents in each case straight-chain or branched alkyl, alkenyl or alkinyl with in each case up to 6 carbon atoms, or, in the case where Z represents an —NH— radical or an alkanesulphonamido radical, also represents hydrogen, or, in the case where Z represents oxygen, also represents one equivalent of an alkali metal, alkaline earth metal or transition metal ion or of an ammonium ion which is optionally substituted by alkyl with 1 to 18 carbon atoms, benzyl or phenethyl and $R^5$ represents hydrogen, or represents in each case straight-chain or branched alkyl, alkenyl or alkinyl with in each case up to 6 carbon atoms, or represents in each case straight-chain or branched alkoxy or alkylsulphonyl with in each case 1 to 6 carbon atoms, or $R^4$ and $R^5$, together with the nitrogen atom to which they are bonded, represent a 3- to 7-membered saturated heterocyclic radical which can contain up to 2 further hetero atoms, in particular nitrogen, oxygen and/or sulphur, $R^6$ represents amino, or represents in each case straight-chain or branched alkyl, alkylamino, dialkylamino or halogenoalkyl with in each case up to 4 carbon atoms in the individual alkyl parts and, in the case of the halogenoalkyl, with up to 9 identical or different halogen atoms and n represents the number 0, 1 or 2, but wherein $R^2$ only represents hydrogen or represents a radical

if $R^1$ does not simultaneously represent unsubstituted alkyl or represent alkyl which is substituted by an alkoximino radical.

In the preferred definition of compounds of the formula (I), halogen in each case represents fluorine, chlorine, bromine or iodine.

Particularly preferred compounds of the formula (I) are those in which $R^1$ represents methyl, ethyl, n- or i-propyl, n-, i-, s- or t-butyl, allyl, butenyl, butinyl or propargyl, in each case optionally mono-, di-, tri-, tetra- or pentasubstituted by identical or different substituents, possible substituents in each case being: fluorine, chlorine, bromine, iodine, cyano, nitro, hydroxyl, methoxy, ethoxy, n- or i-propoxy, amino, methylamino, ethylamino, dimethylamino, diethylamino or di-n-propylamino, carboxyl and a radical

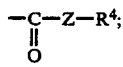

R$^1$ furthermore represents cyclopropyl, cyclopentyl, cyclohexyl or cycloheptyl, in each case optionally mono-, di-, tri-, tetra- or pentasubstituted by identical or different substituents from the group comprising chlorine, bromine, methyl and ethyl, R$^2$ represents hydrogen, or represents methyl, ethyl, n- or i-propyl, n-, i-, s- or t-butyl, allyl, butenyl, propargyl or butinyl, in each case optionally mono-, di- or trisubstituted by identical or different substituents, possible substituents in each case being: fluorine, chlorine, bromine, iodine, cyano, nitro, hydroxyl, methoxy, ethoxy, n- or i-propoxy, amino, methylamino, ethylamino, dimethylamino, diethylamino and din-propylamino; R$^2$ furthermore represents cyclopropyl, cyclopentyl, cyclohexyl or cycloheptyl, in each case optionally mono-, di-, tri-, tetra- or pentasubstituted by identical or different substituents from the group comprising chlorine, bromine methyl and ethyl, or also represents a radical

or

R$^1$ and R$^2$, together with the nitrogen atom to which they are bonded, represent pyrrolidinyl, piperidinyl, perhydroazepinyl or morpholinyl and Ar represents phenyl which is optionally mono-, di-, tri-, tetra- or pentasubstituted by identical or different substituents, or represents 2-pyridyl which is optionally mono-, di-, tri- or tetrasubstituted by identical or different substituents, possible substituents in each case being: cyano, nitro, fluorine, chlorine, bromine, iodine, methyl, ethyl, n- and i-propyl, n-, i-, s- and t-butyl, methoxy, ethoxy, methoxycarbonyl, ethoxycarbonyl, trifluoromethyl, trichloromethyl, dichlorofluoromethyl, difluorochloromethyl, chloromethyl, dichloromethyl, difluoromethyl, pentafluoroethyl, tetrafluoroethyl, trifluorochloroethyl, trifluoroethyl, difluorodichloroethyl, trifluorodichloroethyl, pentachloroethyl, trifluoromethoxy, trichloromethoxy, dichlorofluoromethoxy, difluorochloromethoxy, chloromethoxy, dichloromethoxy, difluoromethoxy, pentafluoroethoxy, tetrafluoroethoxy, trifluorochloroethoxy, trifluoroethoxy, difluorodichloroethoxy, trifluorodichloroethoxy, pentachloroethoxy and a radical —S(O)$_n$—R$^6$, wherein X represents oxygen or sulphur and R$^3$ represents hydrogen, methyl, ethyl, n- or i-propyl, methoxy, ethoxy, methoxymethyl, ethoxymethyl, methoxyethyl, ethoxyethyl, methylthio, ethylthio, methylthiomethyl, methylamino, ethylamino, dimethylamino, allyl, propargyl, butenyl, trifluoromethyl, trichloromethyl, dichlorofluoromethyl, difluorochloromethyl, chloromethyl, iodomethyl, bromomethyl, dichloromethyl, 1-chloroethyl, 2-chloroethyl, 2-bromoethyl or heptafluoro-n-propyl, or represents cyclopropyl, cyclopentyl or cyclohexyl, in each case optionally mono-, di-, tri- or tetrasubstituted by identical or different substituents from the group comprising fluorine, chlorine, bromine, methyl and trifluoromethyl, or represents phenyl, phenoxy, phenylthio or phenylamino, in each case optionally mono-, di- or trisubstituted by identical or different substituents from the group comprising methyl, methoxy, chlorine and trifluoromethyl, Z represents oxygen or a radical

R$^4$ represents methyl, ethyl, n- or i-propyl, n-, i-, s- or t-butyl, allyl or propargyl, or, in the case where Z represents an —NH— radical or an alkanesulphonamido radical, also represents hydrogen, or, in the case where Z represents oxygen, also represents one equivalent of a sodium, potassium, calcium, iron, copper, nickel, tin, magnesium, zinc, manganese, barium, cobalt or ammonium or benzylammonium or alkylammonium salt, wherein alkyl represents methyl, ethyl, n- and i-propyl, n-, i-, s- and t-butyl, n- and i-pentyl, n- and i-hexyl, n- and i-nonyl, n- and i-dodecyl, R$^5$ represents hydrogen, methyl, ethyl, n- or i-propyl, n-, i-, s- or t-butyl, allyl, propargyl, methoxy, ethoxy, n- or i-propoxy, methylsulphonyl or ethylsulphonyl, or R$^4$ and R$^5$, together with the nitrogen atom to which they are bonded, represent pyrrolidinyl, piperidinyl, perhydroazepinyl, piperazinyl or morpholinyl and R$^6$ represents amino, methylamino, ethylamino, dimethylamino, diethylamino, fluorodichloromethyl, difluoromethyl, tetrafluoroethyl, trifluorochloroethyl, trichloromethyl, trichloroethyl, trifluoromethyl, methyl or ethyl and n represents the number 0, 1 or 2, but wherein R$^2$ only represents hydrogen or represents a radical

if R$^1$ does not simultaneously represent unsubstituted alkyl or represent alkyl which is substituted by an alkoximino radical.

Especially preferred compounds of the formula (I) are those in which

R$^1$ represents methyl, ethyl, n- or i-propyl, n-, i-, s- or t-butyl, allyl, butenyl, butinyl or propargyl, in each case optionally mono-, di- or trisubstituted by identical or different substituents, possible substituents in each case being: fluorine, chlorine, bromine, iodine, cyano, nitro, hydroxyl, methoxy, ethoxy, n- and i-propoxy, amino, methylamino, ethylamino, dimethylamino, diethylamino and di-n-propylamino, carboxyl and a radical

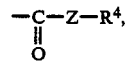

or furthermore represents cyclopropyl, cyclopentyl, cyclohexyl or cycloheptyl, in each case optionally mono-, di-, tri-, tetra- or pentasubstituted by identical or different substituents from the group comprising chlorine, bromine, methyl and ethyl, R² represents hydrogen, or represents methyl, ethyl, n- or i-propyl, n-, i-, s- or t-butyl, allyl, butenyl, propargyl or butinyl, in each case optionally mono-, di- or trisubstituted by identical or different substituents, possible substituents in each case being: fluorine, chlorine, bromine, iodine, cyano, nitro, hydroxyl, methoxy, ethoxy, n- and i-propoxy, amino, methylamino, ethylamino, dimethylamino, diethylamino and di-n-propylamino; or furthermore represents cyclopropyl, cyclopentyl, cyclohexyl or cycloheptyl, in each case optionally mono-, di-, tri-, tetra- or pentasubstituted by identical or different substituents from the group comprising chlorine, bromine, methyl and ethyl, or represents a radical

or

R¹ and R², together with the nitrogen atom to which they are bonded, represent pyrrolidinyl, piperidinyl, perhydroazepinyl or morpholinyl, and Ar represents a radical

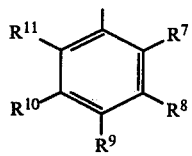

or represents a radical

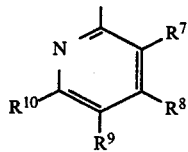

wherein

X represents oxygen or sulphur and

R³ represents hydrogen, methyl, ethyl, n- or i-propyl, methoxy, ethoxy, methoxymethyl, ethoxymethyl, methoxyethyl, ethoxyethyl, methylthio, ethylthio, methylthiomethyl, methylamino, ethylamino, dimethylamino, allyl, propargyl, butenyl, trifluoromethyl, trichloroethyl, dichloro-fluoroethyl, difluorochloroethyl, chloromethyl, iodomethyl, bromomethyl, dichloromethyl, 1-chloroethyl, 2-chloroethyl, 2-bromoethyl or heptafluoro-n-propyl, or represents cyclopropyl, cyclopentyl or cyclohexyl, in each case optionally mono-, di-, tri- or tetrasubstituted by identical or different substituents from the group comprising fluorine, chlorine, bromine, methyl and trifluoromethyl, or represents phenyl, phenoxy, phenylthio or phenylamino, in each case optionally mono-, di- or trisubstituted by identical or different substituents from the group comprising methyl, methoxy, chlorine and trifluoromethyl, Z represents oxygen or a radical

R⁴ represents methyl, ethyl, n- or i-propyl, n-, i-, s- or t-butyl, allyl or propargyl, or, in the case where Z represents an —NH— radical or represents an alkanesulphonamido radical, also represents hydrogen, or, in the case where Z represents oxygen, also represents on eequivalent of a sodium, potassium, calcium, iron, copper, nickel, tin, zinc, magnesium, manganese, barium, cobalt or ammonium or benzylammonium or alkylammonium salt, wherein alkyl represents methyl, ethyl, n- and i-propyl, n-, i-, s- and t-butyl, n- and i-pentyl, n- and i-hexyl, n- and i-nonyl, n- and i-dodecyl, R⁵ represents hydrogen, methyl, ethyl, n- or i-propyl, n-, i-, s- or t-butyl, allyl, propargyl, methoxy, ethoxy, n- or i-propoxy, methylsulphonyl or ethylsulphonyl, or R⁴ and R⁵, together with the nitrogen atom to which they are bonded, represent pyrrolidinyl, piperidinyl, perhydroazepinyl, piperazinyl or morpholinyl, R⁶ represents trifluoromethyl, fluorodichloromethyl, difluorochloromethyl, trichloromethyl or trichloroethyl, or represents methyl or ethyl, R⁷ represents fluorine, chlorine, bromine, methyl or ethyl, R⁸, R¹⁰ and R¹¹ independently of one another in each case represent hydrogen, fluorine, chlorine, bromine, methyl or ethyl, R⁹ represents cyano, nitro, fluorine, chlorine, bromine, methyl, ethyl, n- or i-propyl, n-, i-, s- or t-butyl, methoxy, ethoxy or n- or i-propoxy, or represents trifluoromethyl, trichloromethyl, dichlorofluoromethyl, difluorochloromethyl, chloromethyl, dichloromethyl, difluoromethyl, pentafluoroethyl, tetrafluoroethyl, trifluorochloroethyl, trifluoroethyl, difluorodichloroethyl, trifluorodichloroethyl or pentachloroethyl, or represents trifluoromethoxy, trichloromethoxy, dichlorofluoromethoxy, difluorochloromethoxy, chloromethoxy, dichloromethoxy, difluoromethoxy, pentafluoroethoxy, tetrafluoroethoxy, trifluorochloroethoxy, trifluoroethoxy, difluorodichloroethoxy, trifluorodichloroethoxy or pentachloroethoxy, or represents a radical —S(O)$_n$—R⁶, wherein n and R⁶ have the abovementioned meaning, and n represents the number 0, 1 or 2, but wherein R² only represents hydrogen or a radical

if R¹ does not simultaneously represent unsubstituted alkyl or represent alkyl which is substituted by an alkoximino radical.

The 1-aryl-4-nitro-pyrazoles of the general formula (I) listed in the following table may be mentioned specifically, in addition to the compounds mentioned in the preparation examples:

TABLE 1
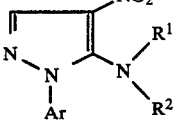
TABLE 1-continued
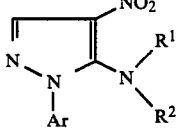

TABLE 1-continued

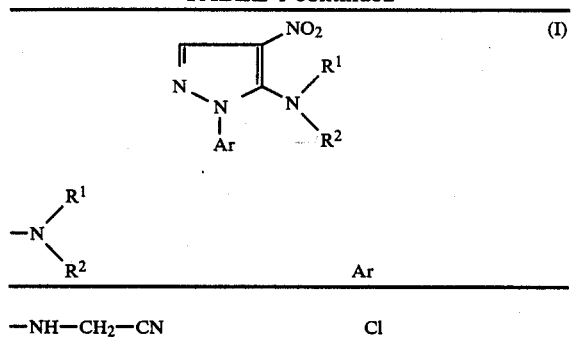

| —N(R¹)(R²) | Ar |
|---|---|
| —NH—CH₂—CN | 3-Cl, 2-(pos), 5-CF₃ pyridine |
| —NH—CH₂—CO—NH—(CH₂)₂—CH₃ | 2-Cl, 4-OCF₃ phenyl |
| —N(COCH₃)(CH₂COOCH₃) | 2,6-diCl, 4-SO₂CF₃ phenyl |
| —NH—CH₂—COOH | 2,6-diCl, 4-SO₂CF₃ phenyl |
| —NH—CH₂—COO⁻Na⁺ | 2,6-diCl, 4-CF₃ phenyl |
| —NH—CH₂—COO—CH(CH₃)₂ | 2,6-diCl, 4-SO₂CF₃ phenyl |
| —NH—CH₂—CN | 2,6-diCl, 4-CF₃ phenyl |
| —NH—CH₂—CH₂—COOCH₃ | 3-Cl, 2-(pos), 5-CF₃ pyridine |

TABLE 1-continued

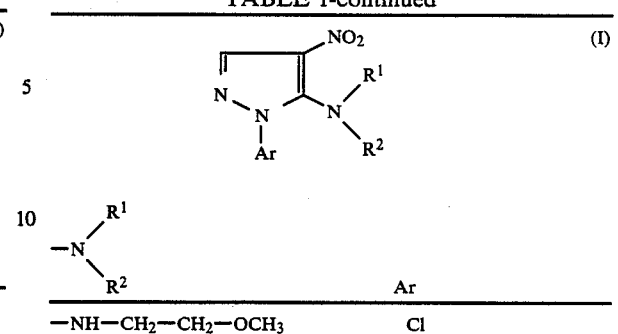

| —N(R¹)(R²) | Ar |
|---|---|
| —NH—CH₂—CH₂—OCH₃ | 2,4-diCl phenyl |
| —NH—CH₂—CH₂—OCH₃ | 2-Cl, 4-CF₃ phenyl |
| —NH—CH₂—CH₂—OH | 2-Br, 4-CF₃, 6-Cl phenyl |
| —NH—CH₂—CH₂—OC₂H₅ | 2-Br, 4-CF₃ phenyl |
| —N(CH₃)(CH₂CH₂OCH₃) | 2,6-diBr, 4-CF₃ phenyl |
| —N(CH₃)₂ | 2-Br, 4-SCF₃ phenyl |
| —N(CH₃)₂ | 2,6-diCl, 4-SCF₃ phenyl |
| —N(pyrrolidine) | 2-Cl, 4-OCF₃ phenyl |

TABLE 1-continued

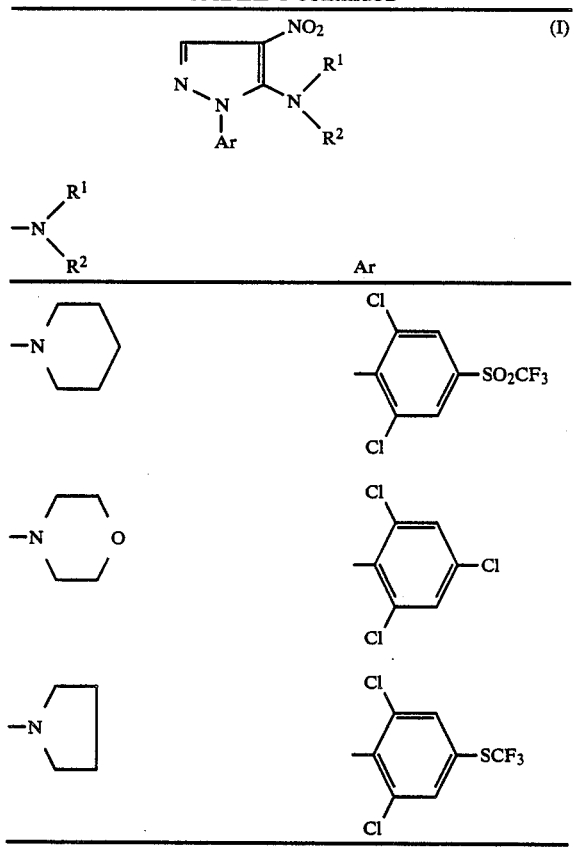

If, for example, 5-chloro-4-nitro-1-(2,4,6-trichlorophenyl)-pyrazole and 2-methoxyethylamine are used as starting substances, the course of the reaction in process (a) according to the invention can be represented by the following equation:

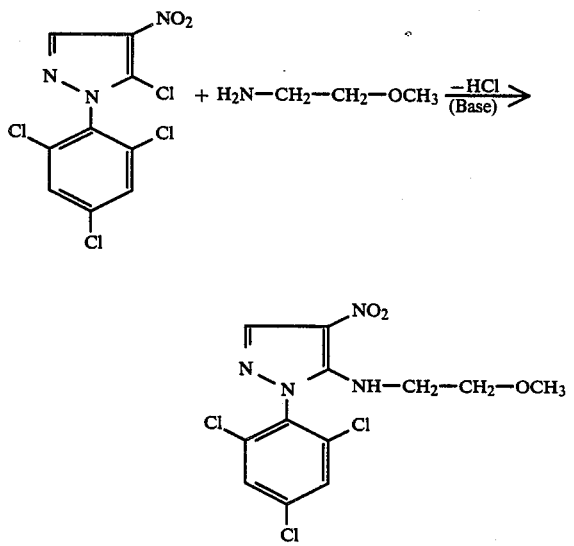

If, for example, 5-propionamideo-4-nitro-1-(2,6-dichloro-4-trifluoromethyl-phenyl)-pyrazole and ethylα-bromophropionate are used as starting substances, the course of the reaction in process (b) according to the invention can be represented by the following equation:

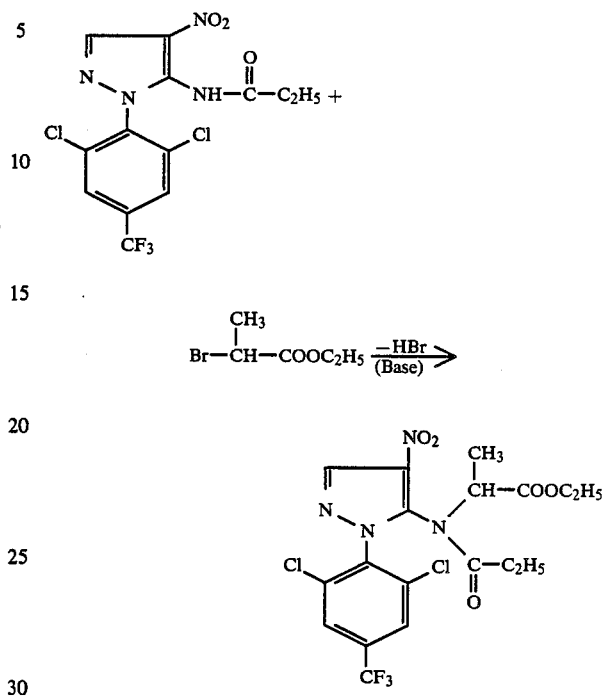

If, for example, 5-(methoxycarbonylmethyl)-acetamido-4-nitro-1-(3-chloro-5-trifluoromethylpyrid-2-yl)-pyrazole is used as the starting compound, the course of the reaction in process (c) according to the invention can be represented by the following equation:

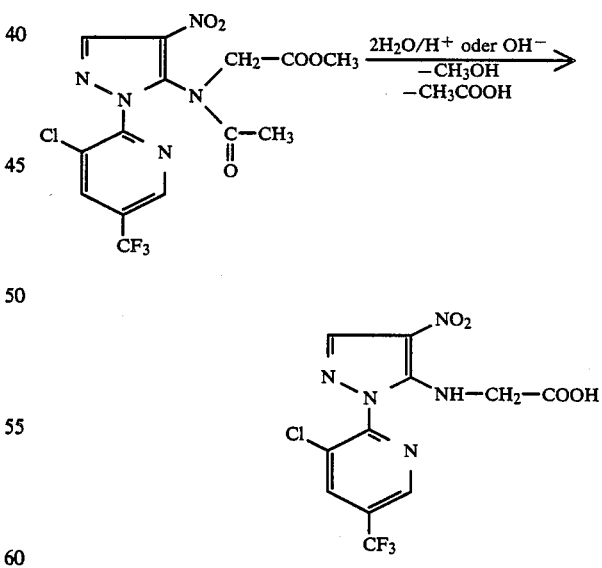

If, for example, N-[4-nitro-1-(2,6-dichloro-4-trifluoromethylthio-phenyl)-pyrazol-5-yl]-aminoacetic acid and propargyl alcohol are used as starting substances and thionyl chloride is used as the reaction auxiliary, the course of the reaction in process (d) according to the invention can be represented by the following equation:

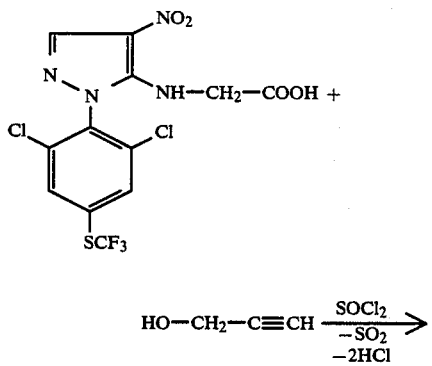

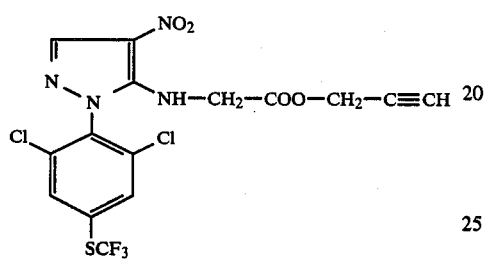

Formula (II) provides a general defnition of the 5-halogeno-4-nitro-1-aryl-pyrazoles required as starting substances for carrrying out process (a) according to the invention. In this formula (II), Ar preferably represents those radicals which have already been mentioned as preferred for this substituent in connection with the description of the substances of the formula (I) according to the invention. Hal preferably represents chlorine or bromine.

The 5-halogeno-4-nitro-1-aryl-pyrazoles of the formula (II) are the subject of commonly assigned application Ser. No. 816,643, filed Jan. 6, 1986, now U.S. Pat No. 4,681,618 and Ser. No. 816,643, filed May 22, 1986, now U.S. No. 4,772, 312, corresponding to German Patent Applications Nos. 3,501,323 of Jan. 17, 1985 and 3,520,330 of June 7, 1985 respectively.

They are obtained, for example, by a process in which 5-amino-1-aryl-pyrazoles of the formula (VI)

in which
Ar has the abovementioned meaning,
are diazotized with nitrite compounds of the formula (VII)

$$R^{12}-O-N=O \qquad (VII)$$

in which
$R^{12}$ represents hydrogen or alkyl or represents an alkali metal cation,
in the customary manner in the presence of a hydrogen halide acid, such as, for example, hydrochloric acid or hydrobromic acid, or in the presence of a haloform, such as, for example, chloroform or bromoform, at temperatures between −20° C. and +80° C. (compare, for example, "Organikum" 15th edition, VEB Deutscher Verlag der Wissenschaften, Berlin 1981, page 652 et seq.; J. Chem. Soc. C, 1966, 1249 or Rev. Latinoam. Quim. 13, 100-102 [1982]).

The 5-amino-1-aryl-pyrazoles of the formula (VI) are known in some cases (compare, for example, U.S. Ser. No. 690,347, filed Jan. 10, 1985, now U.S. Pat. No. 4,674,533, corresponding to German Published Specification No. 3,402,308) and some of them are the subject of commonly assigned U.S. application Ser. No. 866,638, filed May 22, 1986, now U.S. Pat. No. 4,772,312, corresponding to German Patent application No. 3,520,330 of June 7, 1985.

They are obtained, for example, by a process in which aryl-hydrazines of the formula (VIII)

$$Ar-NH-NH_2 \qquad (VIII)$$

in which
Ar has the abovementioned meaning,
and 2-halogenoacrylonitriles of the formula (IX)

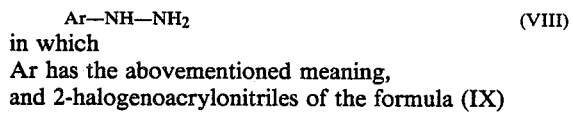

in which
$Hal^1$ represents halogen, in particular chlorine or bromine,
are either reacted initially in a 1st stage, if appropriate in the presence of a diluent, such as, for example, glacial acetic acid or ethanol, and if approprate in the presence of a reaction auxiliary, such as, for example, sodium acetate, at temperatures between −20° C. and +20° C., to give the arylhydrazine derivatives of the formula (X)

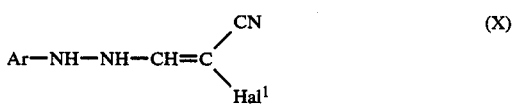

in which
Ar and $Hal^1$ have the abovementioned meaning,
and these are cyclized in a 2nd stage, if appropriate in the presence of a diluent, such as, for example, ethylene glycol monoethyl ether, and if appropriate in the presence of an acid catalyst, such as, for example, sulphuric acid or phosphoric acid, at temperatures between +50° C. and 150° C., or are cyclized directly in one reaction step, without isolation of the intermediate stage of the formula (X), if appropriate in the presence of a diluent, such as, for example, ethylene glycol monoethyl ether or ethanol, at temperatures between +50° C. and +150° C., and the 4-unsubstituted 5-aminopyrazoles thus obtainable, of formula (XI)

in which
Ar has the abovementioned meaning
are nitrated in a subsequent reaction with a nitrating agent, such as, for example, nitric acid, if appropriate in the presence of a diluent, such as, for example, glacial acetic acid, and if appropriate in the presence of a reaction auxiliary, such as, for example, acetic anhydride, at temperatures between −20° C. and +50° C. If appropriate, it may thereby be advantageous for the amino group in the 5-position of the pyrazole ring to be protected before the nitration reaction with the aid of the customary protective group technique, for example by acylation, and for the amino-protective group to be split off again, likewise in the customary manner, for example by hydrolysis with an aqueous or alcoholic base, when the nitration has been carried out.

The arylhydrazines of the formula (VIII) are known (compare, for example, U.S. Pat. No. 4,127,575; U.S. Pat. No. 3,609,158; DE-OS (German Published Specification) No. 2,558,399; and J. Chem. Soc. C, 1971, 167–174), or they can be obtained by known processes in a simple analogous manner (compare, for example, Houben-Weyl "Methoden der organischen Chemie" ("Methods of Organic Chemistry") Volume X/2, page 203, Thieme Verlag Stuttgart, 1967), by a procedure in which, for example, the known anilines or pyridylamines of the formula (XII)

Ar—NH$_2$        (XII)

in which
Ar has the abovementioned meaning,
are reacted with sodium nitrite in the presence of an acid, such as, for example, sulphuric acid, and the products are then reacted with tin-II chloride, likewise in the presence of an acid, such as, for example, hydrochloric acid, at temperatures between −20° C. and +80° C., or by a process in which halogenoaromatics of the formula (XIII)

Ar—Hal$^2$        (XIII)

in which
Ar has the abovementioned meaning and
Hal$^2$ represents halogen, in particular fluorine, chlorine or bromine,
are reacted with hydrazine hydrate, if appropriate in the presence of a diluent, such as, for example, pyridine or dioxane, at temperatures between 0° C. and 150° C.

The nitrite compounds of the formula (VII), the arylhydrazines of the formula (VIII), the 2-halogenoacrylonitriles of the formula (IX), the anilines and pyridylamines of the formula (XII) and the halogenoaromatics of the formula (XIII) are generally known compounds of organic chemistry.

Formula (III) provides a general definition of the amino compounds furthermore required as starting substances for carrying out process (a) according to the invention. In this formula (III), R$^1$ and R$^2$ preferably represent those radicals which have already been mentioned as preferred for these substituents in connection with the description of the substances of the formula (I) according to the invention. The amino compounds of the formula (III) are generally known compounds of organic chemistry.

Formula (Ia) provides a general definition of the 5-amino-4-nitro-1-aryl-pyrazoles required as starting substances for carrying out process (b) according to the invention. In this formula (Ia), R$^2$ and Ar preferably represent those radicals which have already been mentioned as preferred for these substituents in connection with the description of the substances of the formula (I) according to the invention.

The 5-amino-4-nitro-1-aryl-pyrazoles of the formula (Ia) are known in some cases (compare DE-OS (German Published Specification) No. 3,402,308, supra, some of them are the subject of previous Patent Application DE-P No. 3,520,330, supra, and some of them are compounds according to the invention and are obtainable with the aid of processes (a), (b) or (c) according to the invention.

Formula (IV) provides a general definition of the alkylating agents furthermore required as starting substances for carrying out process (b) according to the invention. In this formula (IV), R$^1$ preferably represents those radicals which have already been mentioned as preferred for these substituents in connection with the description of the substances of the formula (I) according to the invention. A preferably represents halogen, in particular chlorine, bromine or iodine, or represents in each case optionally substituted alkylsulphonyloxy, alkoxysulphonyloxy or arylsulphonyloxy, such as, for example, methanesulphonyloxy, methoxysulphonyloxy or p-toluenesulphonyloxy.

The alkylating agents of the formula (IV) are generally known compounds of organic chemistry.

Formula (Ic) provides a general definition of the 5-acylamino-4-nitro-1-aryl-pyrazoles required as starting substances for carrying out process (c) according to the invention. In this formula (Ic), R$^1$, R$^3$ and Ar preferably represent those radicals which have already been mentioned as preferred for these substituents in connection with the description of the substances of the formula (I) according to the invention.

The 5-acylamino-4-nitro-1-aryl-pyrazoles of the formula (I c) are known in some cases (compare DE-OS (German Published Specification) No. 3,402,308, supra, some of them are the subject of previous Patent Application DE-P No. 3,520,330, supra, and some of them are compounds according to the invention and are obtainable with the aid of process (b) according to the invention.

They are obtained, for example, by a procedure in which 5-amino-1-aryl-pyrazoles of the formula (VI)

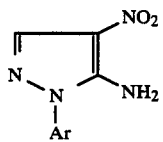

(VI)

in which
Ar has the abovementioned meaning,
are initially acylated in a 1st stage with acylating agents of the formula (XIV)

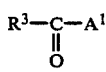

(XIV)

in which
R$^3$ has the abovementioned meaning and
A$^1$ represents an electron-withdrawing leaving group, such as, for example, halogen or a radical

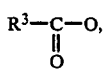

or with an isocyanate of the formula (XV)

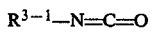 (XV)

in which

R³⁻¹ represents alkyl, or represents optionally for substituted aryl, and preferably represents alkyl with 1 to 4 carbon atoms, or represents phenyl which is optionally monosubstituted or polysubstituted by identical or different substituents from the group comprising fluorine, chlorine, bromine, iodine, alkyl with 1 to 4 carbon atoms and halogenoalkyl with 1 to 4 carbon atoms and 1 to 5 halogen atoms, if appropriate in the presence of a diluent, such as, for example, methylene chloride or acetonitrile, and if appropriate in the presence of an acid-binding agent, such as, for example, potassium carbonate or triethylamine, in the customary manner at temperatures between $-20°$ C. and $+120°$ C., and the 5-acyl-amino-pyrazoles thus obtainable, of the formula (XVI)

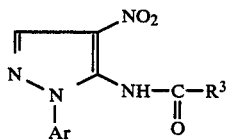 (XVI)

in which $R^3$ and Ar have the abovementioned meaning, are alkylated in a 2nd stage with alkylating agents of the formula (IV)

 (IV)

in which $R^1$ and A have the abovementioned meaning, as described for process (b) according to the invention.

The acylating agents of the formula (XIV) and the alkylating agents of the formula (IV) are generally known compounds of organic chemistry.

Formula (Ie) provides a general definition of the pyrazolylcarboxylic acid derivatives required as starting substances for carrying out process (d) according to the invention. In this formula (Ie), Ar preferably represents those radicals which have already been mentioned as preferred for this substituent in connection with the description of the substances of the formula (I) according to the invention. Y preferably represents straight-chain or branched alkylene, alkenylene or alkinylene with in each case up to 8 carbon atoms, and preferably represents methylene, ethylene, propylene or butylene, propenylene or butenylene or propinylene or butinylene.

The pyrazolylcarboxylic acid derivatives of the formula (Ie) are compounds according to the invention and are obtainable with the aid of process (c) according to the invention, in particular by a procedure in which the 5-acylamino-4-nitro-1-aryl-pyrazoles obtainable by process (b), of the formula (Ic-1)

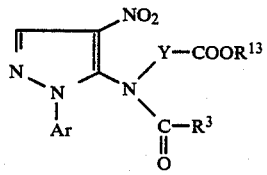 (Ic-1)

in which
$R^3$, Ar and Y have the abovementioned meaning and $R^{13}$ represents methyl or ethyl,
are simultaneously hydrolyzed and deacylated with bases, such as, for example, aqueous sodium hydroxide solution, if appropriate in the presence of a diluent, such as, for example, methanol or ethanol, at temperatures between 0° C. and 120° C.

Formula (V) provides a general definition of the alcohols, amines or salts furthermore required as starting substances for carrying out process (d) according to the invention. In this formula (V), $R^4$ and Z preferably represent those radicals which have already been mentioned as preferred for these substituents in connection with the description of the substances of the formula (I) according to the invention.

The alcohols, amines and salts of the formula (V) are generally known compounds of organic chemistry.

Possible diluents for carrying out preparation process (a) are inert organic solvents. These include, in particular, aliphatic or aromatic, optionally halogenated hydrocarbons, such as, for example, benzine, benzene, toluene, xylene, chlorobenzene, petroleum ether, hexane, cyclohexane, methylene chloride, chloroform and carbon tetrachloride, ethers, such as diethyl ether, dioxane, tetrahydrofuran or ethylene glycol dimethyl or diethyl ether, ketones, such as acetone or butanone, nitriles, such as acetonitrile or propionitrile, amides, such as dimethylformamide, dimethylacetamide, N-methylformanilide, N-methylpyrrolidone or hexamethylphosphoric acid triamide, esters, such as ethyl acetate, or sulphoxides, such as dimethylsulphoxide.

If appropriate, process (a) according to the invention can be carried out in the presence of a suitable acid-binding agent. Possible acid-binding agents are all the customary inorganic or organic bases. These include, for example, alkali metal hydroxides, such as sodium hydroxide or potassium hydroxide, alkali metal carbonates, such as sodium carbonate or sodium bicarbonate, and tertiary amines, such as triethylamine, N,N-dimethylaniline, pyridine, N,N-dimethylaminopyridine, diazabicyclooctane (DABCO), diazabicyclononene (DBN) or diazabicycloundecene (DBU).

However, it is also possible for a corresponding excess of the amine of the formula (III) employed as a reaction partner simultaneously to be used as the acid-binding agent.

The reaction temperatures can be varied within a substantial range in carrying out process (a) according to the invention. The reaction is in general carried out at temperatures between $-20°$ C. and $+200°$ C., preferably at temperatures between 0° C. and $+150°$ C.

For carrying out process (a) according to the invention, in general 1.0 to 10.0 moles, preferably 1.0 to 5.0 moles, of amine of the formula (III) are employed per mole of 5-halogeno-4-nitro-1-aryl-pyrazole of the formula (II). The reaction is carried out and the reaction products of the formula (I) are worked up and isolated by generally customary processes.

Possible diluents for carrying out process (b) according to the invention are inert organic solvents. These include, in particular, aliphatic or aromatic, optionally halogenated hydrocarbons, such as, for example, benzine, benzene, toluene, xylene, chlorobenzene, petroleum ether, hexane, cyclohexane, methylene chloride, chloroform and carbon tetrachloride, ethers, such as diethyl ether, dioxane, tetrahydrofuran or ethylene glycol dimethyl or diethyl ether, ketones, such as acetone or butanone, nitriles, such as acetonitrile or propionitrile, amides, such as dimethylformamide, dimethylacetamide, N-methylformanilide, N-methylpyrrolidone of hexamethylphosphoric acid triamide, esters, such as ethyl acetate, or sulphoxides, such as dimethylsulphoxide.

If appropriate, process (b) according to the invention can also be carried out in a two-phase system, such as, for example, water/toluene or water/methylene chloride, if appropriate in the presence of a phase transfer catalyst. Examples which may be mentioned of such catalysts are: tetrabutylammonium iodide, tetrabutylammonium bromide, tributyl-methylphosphonium bromide, trimethyl-$C_{13}/C_{15}$-alkylammonium chloride, dibenzylammonium methylsulphate, dimethyl-$C_{12}/C_{14}$-alkyl-benzylammonium chloride, tetrabutylammonium hydroxide, 15-crown-5, 18-crown-6, triethylbenzylammonium chloride and trimethylbenzylammonium chloride.

Possible acid-binding agents for carrying out preparation process (b) are all the inorganic and organic bases which can usually be employed. Bases which are preferably used are alkali metal hydrides, hydroxides, amides, carbonates or bicarbonates, such as, for example, sodium hydride, sodium amide, sodium hydroxide, sodium carbonate or sodium bicarbonate, or also tertary amines, such as, for example, triethylamine, N,N-dimethylaniline, pyridine, 4-(N,N-dimethylamino)pyridine, diazabicyclooctane (DABCO), diazabicyclononene (DBN) or diazabicycloundecene (DBU).

The reaction temperatures can be varied within a substantial range in carrying out preparation process (b). The reaction is in general carried out between $-20°$ C. and $+150°$ C., preferably between $0°$ C. and $+100°$ C.

For carrying out preparation process (b), in general 1.0 to 20.0 moles, preferably 1.0 to 15.0 moles, of alkylating agent of the formula (IV) and, if appropriate, 1.0 to 3.0 moles, preferably 1.0 to 2.0 moles, of acid-binding agent and 0.01 to 1.0 mole of phase transfer catalyst are employed per mole of 5-amino-4-nitro-1-arylpyrazole of the formula (Ia). The reaction is carried out and the reaction products of the formula (I) are worked up and isolated in the generally customary manner.

Possible diluents for carrying out process (c) according to the invention are inert organic or inorganic solvents. The organic solvents listed for process (b) may be mentioned in particular. Moreover, alcohols, such as methanol or ethanol or mixtures thereof with water, are particularly preferred.

Process (c) is carried out either in the presence of a strong acid, such as, for example, hydrochloric acid, trifluoroacetic acid or hydrobromic acid in glacial acetic acid, or in the presence of a base. Preferred bases are aqueous solutions of sodium hydroxide or potassium hydroxide.

The reaction temperatures can be varied within a substantial range in carrying out process (c) according to the invention. The reaction is in general carried out at temperatures between $-20°$ C. and $+150°$ C., preferably at temperatures between $0°$ C. and $+120°$ C.

For carrying out process (c) according to the invention, in general 1 to 30 moles, preferably 1 to 15 moles, of acid or base are employed per mole of 5-acylamino-4-nitro-1-aryl-pyrazole of the formula (I c). The reaction is carried out and the reaction products of the formula (Ib) are worked up and isolated in the generally customary manner.

Possible diluents for carrying out process (d) are inert organic solvents. These include, in particular, aliphatic or aromatic, optionally halogenated hydrocarbons, such as, for example, benzine, benzene, toluene, xylene, chlorobenzene, petroleum ether, hexane, cyclohexane, methylene chloride, chloroform and carbon tetrachloride, ethers, such as diethyl ether, dioxane, tetrahydrofuran or ethylene glycol dimethyl or diethyl ether, ketones, such as acetone or butanone, nitriles, such as acetonitrile or propionitrile, amides, such as dimethylformamide, dimethylacetamide, N-methylformanilide, N-methylpyrrolidone or hexamethylphosphoric acid triamide, esters, such as ethyl acetate, or sulphoxides, such as dimethylsulphoxide. If alcohols or amines in liquid form are used as reaction partners of the formula (V), it is also possible for these to be simultaneously employed as the soleent in a corresponding excess.

Organic or aqueous solvents or organic-aqueous solvent mixtures are suitable for salt formation according to process (d), that is to say in the cases where $R^4$ in formula (V) represents an inorganic or organic cation and Z represents oxygen. Alcohols, such as methanol, ethanol or propanol or mixtures thereof with water, as well as pure water, are preferably used heFe as the diluent.

If appropriate (that is to say in cases where an esterification or amidation reaction takes place), process (d) according to the invention is carried out in the presence of a suitable reaction auxiliary. Possible reaction auxiliaries are in principle all the reaction auxiliaries which can usually be employed for esterifications and amidations. Examples which may be mentioned are agents which form acid halides, such as thionyl chloride, phosphorus trichloride, phosphorus pentachloride or phosphorus oxychloride, or active ester components, such as N-hydroxy-succinimide, agents which form anhydrides, such as 4-nitrophenyl chloroformate, or customary condensing agents, such as dicyclohexylcarbodiimide (DCC), triphenylphosphine mixed with carbon tetrachloride, N,N'-carbonyldiimidazole or N-ethoxycarbonyl-2-ethoxy-dihydroquinoline (EEDQ).

If appropriate, process (d) according to the invention can be carried out in the presence of a suitable acid-binding agent. Possible acid-binding agents are all the inorganic or organic bases which can usually be employed. These include, for example, alkali metal hydroxides, such as sodium hydroxide or potassium hydroxide, alkali metal carbonates, such as sodium carbonate, and tartieary amines, such as triethylamine, N,N-dimethylaniline, pyridine, N,N-dimethylaminopyridine, diazabicyclooctane (DABCO); diazabicyclononene (DBN) or diazabicycloundecene (DBU). A corresponding excess of an amine or hydroxide simultaneously used as the reaction partner of the formula (V) can also serve, if appropriate, as the acid-binding agent.

The reaction temperatures can be varied within a substantial range in carrying out process (d) according to the invention. The reaction is in general carried out at temperatures between $-20°$ C. and $+150°$ C., preferably at temperatures between $0°$ C. and $+100°$ C.

For carrying out process (d) according to the invention, in general 1.0 to 20.0 moles, preferably 1.0 to 10.0 moles, of alcohol, amine or hydroxide of the formula (V), 1.0 to 5.0 moles, preferably 1.0 to 2.0 moles, of reaction auxiliary and, if appropriate, 1.0 to 2.0 moles of acid-binding agent are employed per mole of pyrazolyl-carboxylic acid derivative of the formula (Ie).

In cases where an esterification or amidation reaction takes place, it is advantageous first to prepare an activated complex (acid halide, active ester, mixed anhydride and the like) from the pyrazolylcarboxylic acid derivatives of the formula (Ie) and the reaction auxiliary by customary processes, and this can then be isolated, if appropriate, and reacted with the alcohol or amine of the formula (V) either in a separate reaction step or in a one-pot process. The addition of the acid-binding agent here can be beneficial either in the 1st stage for formation of the activated complex or in the 2nd stage for reaction thereof, depending on the reaction auxiliary used. The reaction is carried out and the reaction products of the formula (Id) are worked up and isolated by generally customary processes.

The active compounds according to the invention can be used as defoliants, desiccants, agents for destroying broad-leaved plants and, especially, as weedkillers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The active compounds according to the invention can be used here with particularly good success for selectively combating monocotyledon and dicotyledon weeds in monocotyledon crops, such as, for example, cotton, barley or wheat.

When applied in appropriate amounts, the active compounds according to the invention in addition also show insecticidal and fungicidal activities and can be used, for example, for combating leaf insects or hygiene pests and pests of stored products, or for combating rice diseases, such as, for example, against the rice spot disease causative organism (*Pyricularia oryzae*).

The active compounds according to the invention moreover engage in the metabolism of the plants and can therefore be employed as growth regulators.

Experience to date of the mode of action of plant growth regulators has shown that an active compound can also exert several different actions on plants. The actions of the compounds depend essentially on the point in time at which they are used, reative to the stage of development of the plant, and on the amounts of active compound applied to the plants or their environment and the way in which the compounds are applied. In every case, growth regulators are intended to influence the crop plants in the particular manner desired.

Plant growth-regulating compounds can be employed, for example, to inhibit vegetative growth of the plants. Such inhibition of growth is, inter alia, of economic interest in the case of grasses, since it is thereby possible to reduce the frequency of cutting the grass in ornamental gardens, parks and sportsgrounds, at verges, at airports or in fruit orchards. The inhibition of growth of herbaceous and woody plants at verges and in the vicinity of pipelines or overland lines or, quite generally, in areas in which heavy additional growth of plants is undesired, is also of importance.

The use of growth regulators to inhibit the growth in length of cereals is also important. The danger of bending ("lodging") of the plants before harvesting is thereby reduced or completely eliminated. Furthermore, growth regulators can strengthen the stem of cereals, which again counteracts lodging. Use of growth regulators for shortening and strengthening the stem enables higher amounts of fertilizer to be applied to increase the yield, without danger of the cereal lodging.

In the case of many crop plants, inhibition of the vegetative growth makes denser planting possible, so that greater yields per area of ground can be achieved. An advantage of the smaller plants thus produced is also that the crop can be worked and harvested more easily.

Inhibition of the vegetative growth of plants can also lead to increases in yield, since the nutrients and assimilates benefit blossoming and fruit formation to a greater extent than they benefit the vegetative parts of plants.

Promotion of vegetative growth can also frequently be achieved with growth regulators. This is of great utility if it is the vegetative parts of the plants which are harvested. Promoting the vegetative growth can, however, also simultaneously lead to a promotion of generative growth, since more assimilates are formed, so that more fruit, or larger fruit, is obtained.

Increases in yield can in some cases be achieved by affecting the plant metabolism, without noticeable changes in vegetative growth. A change in the composition of plants, which in turn can lead to a better quality of the harvested products, can furthermore be achieved with growth regulators. Thus it is possible, for example, to increase the content of sugar in sugar beet, sugar cane, pineapples and citrus fruit or to increase the protein content in soya or cereals. Using growth regulators it is also possible, for example, to inhibit the degradation of desired constituents, such as, for example, sugar in sugar beet or sugar cane, before or after harvesting. It is also possible favorably to influence the production or the efflux of secondary plant constituents. The stimulation of latex flux in rubber trees may be mentioned as an example.

Parthenocarpous fruit can be formed under the influence of growth regulators. Furthermore, the gender of the flowers can be influenced. Sterility of the pollen can also be roduced, which is of great importance in the breeding and preparation of hybrid seed.

Branching of plants can be controlled by using growth regulators. On the one hand, by breaking the apical dominance the development of side shoots can be promoted, which can be very desirable, especially in the cultivation of ornamental plants, also in connection with growth inhibition. On the other hand, however, it is also possible to inhibit the growth of side shoots. There is great interest in this action, for example, in the cultivation of tobacco or in the planting of tomatoes.

The amount of leaf on plants can be controlled, under the influence of growth regulators, so that defoliation of the plants at a desired point in time is achieved. Such defoliation is of great importance in the mechanical harvesting of cotton, but is also of interest for facilitating harvesting in other crops, such as, for example, in viticulture. Defoliation of the plants can aLso be carried out to lower the transpiration of plants before they are transplanted.

The shedding of fruit can also be controlled with growth regulators. On the one hand, it is possible to prevent premature shedding of fruit. However, on the other hand, shedding of fruit, or even the fall of blossom, can be promoted up to a certain degree ("thinning out") in order to interrupt the alternance. By alternance there is understood the peculiarity of some varieties of fruit to produce very different yields from year to year, for endogenic reasons. Finally, using growth regulators it is possible to reduce the forces required to detach the fruit at harvest time so as to permit mechanical harvesting or facilitate manual harvesting.

Using growth regulators, it is furthermore possible to achieve an acceleration or retajation of ripening of the harvest product, before or after harvesting. This is of particular advantage, since it is thereby possible to achieve optimum adaptation to market requirements. Furthermore, growth regulators can at times improve the coloration of fruit. In addition, concentrating the ripening within a certain period of time is also achievable with the aid of growth regulators. This provides the preconditions for being able to carry out complete mechanical or manual harvesting in only a single pass, for example in the case of tobacco, tomatoes or coffee.

Using growth regulators, it is furthermore possible to influence the latent period of seeds or buds of plants, so that the plants, such as, for example, pineapple or ornamental plants in nurseries, germinate, shoot or blossom at a time at which they normally show no readiness to do so. Retarding the shooting of buds or the germination of seeds with the aid of growth regulators can be desirable in regions where frost is a hazard, in order to avoid damage by late frosts.

Finally, resistance of plants to frost, drought or a high salt content in the soil can be induced with growth regulators. Cultivation of plants in regions which are usually unsuitable for this purpose thereby becomes possible.

The active compounds can be converted to the customary formulations, such as solutions, emulsions, wettable powders, suspensions, powders, dusting agents, pastes, soluble powders, aerosols, granules, suspension-emulsion concentrates, natural and synthetic materials impregnated with active compound and very fine capsules in polymeric substances.

These formulations are produced in known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkyl naphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silicic acid, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, oorn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl-sulphonates, alkylsulphates, arylsulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as naturally occurring phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention, as such or in the form of their formulations, can also be used, for combating weeds, as mixtures with known herbicides, finished formulations or tank mixes being possible.

Possible components for the mixtures are known herbicides, such as, for example, 1-amino-6-ethylthio-3-(2,2-dimethylpropyl)-1,3,5-triazine-2,4-(1H,3H)-dione or N-(2-benzothiazolyl)-N,N'-dimethyl-urea, for combating weeds in cereals; 4-amino-3-methyl-6-phenyl-1,2,4-triazin-5(4H)-one for combating weeds in sugar beet and 4-amino-6-(1,1-dimethylethyl)-3-methylthio-1,2,4-triazin-5(4H)-one for combating weeds in soy beans.

Mixtures with N,N-dimethyl-N'-(3-trifluoromethylphenyl)-urea; N,N-dimethyl-N'-(3-chloro-4-methylphenyl)-urea; N,N-dimethyl-N'-(4-isopropylphenyl)-urea; 4-amino-6-t-butyl-3-ethylthio-1,2,4-triazin-5(4H)-one; 2,4-dichlorophenoxyacetic acid; 2,4-dichlorophenoxy-propionic acid; (2-methyl-4-chlorophenoxy)-acetic acid; (4-chloro-2-methylphenoxy)-propionic acid; chloroacetic acid N-(methoxymethyl)-2,6-diethylanilide; 2-ethyl-6-methyl-N-(1-methyl-2-methoxyethyl)-chloroacetanilide; 2,6-dinitro-4-trifluoromethyl-N,N-dipropylaniline; 2-benzyloxyethyl, trimethylsilylmethyl or 2,2-diethoxyethyl 2-[4-(3,5-dichloropyrid-2-yloxy)-phenoxy]-propionate; N-(1-ethylpropyl)-3,4-dimethyl-2,6-dinitroaniline; exo-1-methyl-4-(1-methylethyl)-2-(2-methylphenylmethoxy)-7-oxabicyclo-[2.2.1]-heptane; 2-{4-[[3-chloro-5-(trifluoromethyl)-2-pyridinyl]-oxy]-phenoxy}-propanoic acid and -propanoic acid ethyl ester; S-(2,3,3-trichloroallyl) N,N-diisopropyl-thiolcarbamate; N-methyl-2-(1,3-benzothiazol-2-yloxy)-acetanilide; methyl 5-(2,4-dichlorophenoxy)-2-nitrobenzoate 3,5-diiodo-4-hydroxybenzonitrile; 3-isopropyl-2,1,3-benzothiadiazin-4-one 2,2-dioxide; 2-chloro-N-{[[4-methoxy-6-methyl-1,3,5-triazin-2-yl)-amino]-carbonyl}benzenesulphonamide; 4-ethylamino-2-t-butylamino-6-methylthio-s-triazine; methyl 2-[4-(2,4-dichlorophenoxyphenoxy)phenoxy]-propionate or [(4-amino-3,5-dichloro-6-fluoro-2-pyridinyl)-oxy]-acetic acid or -acetic acid 1-methylheptyl ester, where appropriate, are also of advantage.

Surprisingly, some mixtures also show a synergistic action.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants. They can also be incorporated into the soil before sowing.

The amount of active compound used can vary within a substantial range. It depends essentially on the nature of the desired effect. In general, the amounts used are between 0.01 and 10 kg of active compound per hectare of soil surface, preferably between 0.05 and 5 kg per ha.

When used as growth regulators, the active compounds according to the invention can likewise be present in the formulations as a mixture with other known active compounds, sch as fungicides, insecticides, acaricides and herbicides, and also as mixtures with fertilizers and other growth regulators.

The active compounds can be used in this context as such, in the form of their formulations or in the use forms prepared therefrom, such as ready-to-use solutions, emulsifiable concentrates, emulsions, foams, suspensions, wettable powders, pastes, soluble powders, dusting agents and granules. They are used in the customary manner, for example by watering, spraying, atomizing, scattering, dusting, foaming, coating and the like. Furthermore, it is possible to apply the active compounds in accordance with the ultra-low volume process or to inject the active compound preparation or the active compound itself into the soil. It is also possible to treat the seeds of plants.

When used as plant growth regulators, the amounts applied can likewise be varied within a substantial range. In general, 0.01 to 50 kg, preferably 0.05 to 10 kg, of active compound are used per hectare of soil surface.

As regards the time of application, the growth regulators are applied within a preferred period of time, the exact definition of which depends on the climatic and vegetative circumstances.

The following examples illustrate the preparation and use of the active compounds according to the invention.

PREPARATION EXAMPLES

EXAMPLE 1

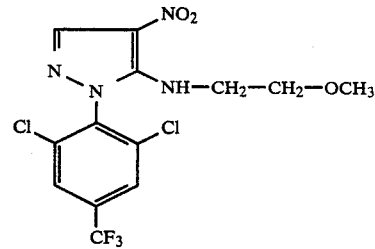

(Process a)

12.0 g (0.03 mole) of 5-bromo-1-(2,6-dichloro-4-trifluoromethylphenyl)-4-nitro-pyrazole and 10 g (0.13 mole) of 2-methoxyethylamine are stirred in 50 ml of dioxane at 50° C. to 60° C. for 12 hours. For working up, the cooled reaction mixture is poured into water and extracted several times with chloroform. The combined organic phases are washed with water, dried over sodium sulphate and concentrated in vacuo and the residue is crystallized with ligroin. 6.6 g (55% of theory) of 1-(2,6-dichloro-4-trifluoromethyl-phenyl)-5-(2-methoxyethylamino)-4-nitro-pyrazole of melting point 85° C.–90° C. are obtained.

Preparation of the starting compound

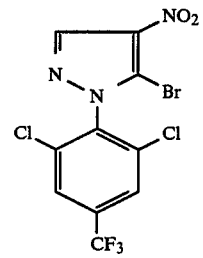

18 ml (0.16 mole) of t-butyl nitrite are added dropwise to 17.1 g (0.05 mole) of 5-amino-4-nitro-1-(2,6-dichloro-4-trifluoromethyl-phenyl)-pyrazole (compare DE-OS (German Published Specification) No. 3,402,308), supra, in 75 ml of bromoform in the course of 15 minutes, with stirring, whereupon the temperature of the reaction mixture rises to 50° C. When the addition has ended, the mixture is stirred at the reflux temperature for a further hour and concentrated in vacuo. 18.0 g (89% of theory) of 1-(2,6-dichloro-4-trifluoromethylphenyl)-4-nitro-5-bromo-pyrazole of melting point 96° C. are obtained.

EXAMPLE 2

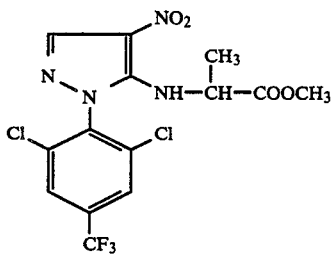

(Process b)

2.8 g (0.02 mole) of potassium carbonate are added to 3.4 g (0.01 mole) of 1-(2,6-dichloro-4-trifluoromethyl-phenyl)-4-nitro-5-amino-pyrazole, dissolved in 30 ml of acetonitrile, and 3.7 g (0.022 mole) of methyl α-bromopropionate, dissolved in 10 ml of acetonitrile, are added dropwise at room temperature in the course of 10 minutes. The reaction mixture is heated under reflux for 2½ hours and filtered hot and the solvent and excess α-bromopropionate are removed by concentration of the filtrate in vacuo. The residue is crystallized from petroleum ether. 3.8 g (88% of theory) of methyl α-{N-[1-(2,6-dichloro-4-trifluoromethyl-phenyl)-4-nitro-pyrazol-5-yl]amino}-propionate of melting point 123° C.-130° C. are obtained.

The 1-aryl-4-nitro-pyrazoles of the formula (I) listed in the following table are obtained in a corresponding manner and in accordance with the general statements on the preparation:

TABLE 2 (I)

| Example No. | $R^1$ | $R^2$ | $-N\begin{smallmatrix}R^1\\R_2\end{smallmatrix}$ | Ar | Physical properties |
|---|---|---|---|---|---|
| 3 | —CH₂—CH₂—OCH₃ | H | — | 2,4,6-trichlorophenyl | m.p. 125° C. |
| 4 | —CH(CH₃)—COOCH₃ | H | — | 2,6-dichloro-4-(SCF₃)-phenyl | m.p. 113° C. |
| 5 | —CH(CH₃)—COOCH₃ | H | — | 2,6-dichloro-4-(OCF₃)-phenyl | ¹H—NMR*: δ = 1,4 (dd,3H) for —CH—CH₃; δ = 8,15 (s,1H) for pyrazole H |
| 6 | —CH₂—CH₂—OH | H | — | 2,6-dichloro-4-CF₃-phenyl | m.p. 127–130° C. |

TABLE 2-continued $$\underset{Ar}{\underset{|}{N}}\!\!-\!\!\underset{\underset{R^2}{|}}{\overset{NO_2}{\underset{|}{N}}}\!\!-\!\!R^1 \quad (I)$$

| Example No. | R¹ | R² | $-N\begin{matrix}R^1\\R_2\end{matrix}$ | Ar | Physical properties |
|---|---|---|---|---|---|
| 7 | —CH₂—CH₂—N(C₂H₅)₂ | H | — | 2,5-Cl₂-4-CF₃-C₆H₂ | ¹H—NMR* δ = 1.01 (t,6H)) for —N(CH₂—CH₃)₂; δ = 8.12 (s,14) for pyrazole H |
| 8 | —CH₂—CH₂—CH₂—OH | H | — | 2,5-Cl₂-4-CF₃-C₆H₂ | m.p. 85-88° C. |
| 9 | —CH₂—CH₂—CH₂—OCH₃ | H | — | 2,5-Cl₂-4-CF₃-C₆H₂ | m.p. 83° C. |
| 10 | —CH(CH₃)—COOCH₃ | H | — | 2,3,5-Cl₃-4-CF₃-C₆H | m.p. 122-126° C. |
| 11 | — | — | pyrrolidin-1-yl | 2,3,5-Cl₃-C₆H₂ | m.p. 154° C. |
| 12 | CH₃ | CH₃ | — | 2,3,5-Cl₃-C₆H₂ | m.p. 123° C. |
| 13 | CH₃ | CH₃ | — | 2,5-Cl₂-4-CF₃-C₆H₂ | m.p. 65-70° C. |

TABLE 2-continued

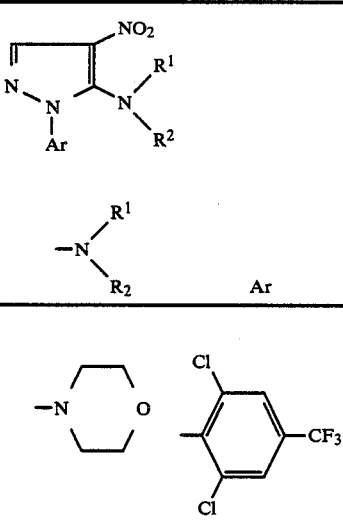
(I)

| Example No. | R¹ | R² | −N$<$R¹/R² | Ar | Physical properties |
|---|---|---|---|---|---|
| 14 | — | — | 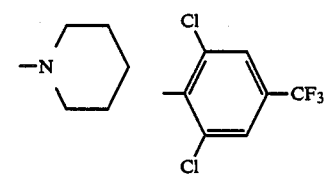 morpholino | 2,6-dichloro-4-CF₃-phenyl | m.p. 120–125° C. |
| 15 | — | — | piperidino | 2,6-dichloro-4-CF₃-phenyl | m.p. 150–155° C. |
| 16 | — | — | pyrrolidino | 2,6-dichloro-4-CF₃-phenyl | m.p. 125–130° C. |
| 17 | —CH₂—CH=CH₂ | H | — | 2,6-dichloro-4-CF₃-phenyl | ¹H—NMR* $\delta = 3.5$ (m,2H) for —NH—(CH₂)—CH=CH₂ $\delta = 8.15$ (s,1H) for (H) on pyrazole |
| 18 | —CH₂—CH₂—CH₂—OC₂H₅ | H | — | 2,6-dichloro-4-CF₃-phenyl | m.p. 75–78° C. |
| 19 | CH₃ | CH₃ | — | 2-chloro-4-bromo-phenyl | ¹H—NMR* $\delta = 2.8$ (s,6H) for —N(CH₃)₂ $\delta = 8.21$ (s,1H) for (H) on pyrazole |

TABLE 2-continued

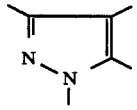

| Example No. | $R^1$ | $R^2$ | $-N\begin{smallmatrix}R^1\\R_2\end{smallmatrix}$ | Ar | Physical properties |
|---|---|---|---|---|---|
| 20 | $-CH_2-CH=CH_2$ | H | — | (2,4,6-trichloro-3-CF$_3$-phenyl) | m.p. 127–132° C. |
| 21 | $-CH(CH_3)-COOC_2H_5$ | H | — | (2,4,6-trichloro-3-CF$_3$-phenyl) | $^1$H—NMR*<br>δ = 1.4 (dd,3H) for $-CH-CH_3$<br>δ = 8.15 (s,1H) for (H) on pyrazole |

*The $^1$H—NMR spectra were recorded in CDCl$_3$ with TMS as the internal standard. The chemical shift δ in ppm is stated.

USE EXAMPLES

The compound shown below was employed as the comparaison substance in the use examples which follows:

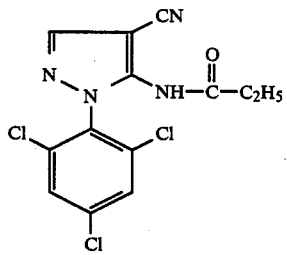
(A)

4-Cyano-5-propionamido-1-(2,4,6-trichloro-phenyl)-pyrazole known from DE-OS (German published specification) No. 3,226,513), supra.

EXAMPLE A

Pre-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0%=no action (like untreated control)
100%=total destruction

In this test, a clearly superior activity and selectivity for useful plants, especially wheat, barley and cotton, compared with the prior art are shown, for example, by the compounds according to the following preparation examples 1 and 13.

EXAMPLE B

Post-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in damage in comparison to the development of the untreated control. The figures denote:

0%=no action (like untreated control)
100%=total destruction

In this test, a clearly superior activity and selectivity for useful plants, especially wheat, compared with the prior art are shown, for example, by the compounds according to the following preparation examples 1, 13, 17, 20 and 21.

EXAMPLE C

Defoliation and desiccation of the leaves of cotton

Solvent: 30 parts by weight of dimethylformamide
Emulsifier: 1 part by weight of polyoxyethylene sorbitane monolaurate To produce a suitable preparation of active compound, 1 part by weight of active compound is mixed with the stated amounts of solvent and emulsifier and the mixture is made up to the desired concentration with water.

Cotton plants are grown in a greenhouse until the 5th secondary leaf has unfolded completely. In this stage, the plants are sprayed with the preparations of active compound until dripping wet. After one week, the shedding of leaves and the desiccation of the leaves are rated, in comparison with the control plants.

The figures of merit have the following meanings:

0 denotes no desiccation of leaves, no shedding of leaves

+ denotes slight desiccation of the leaves, slight shedding of leaves

++ denotes severe desiccation of the leaves, severe shedding of leaves

+++ denotes very severe desiccation of the leaves, very severe shedding of leaves.

In this test, a clearly superior activity compared with the untreated control is shown, for example, by the compounds according to the following preparation examples: 1, 6, 7 and 13.

It will be understood that the specification and examples are illustrative but not limitative of the present invention and that other embodiments within the spirit and scope of the invention will suggest themselves to those skilled in the art.

We claim:

1. A 1-aryl-4-nitro-pyrazole of the formula

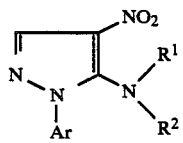

in which $R^1$ represents alkyl, alkenyl or alkinyl with up to 8 carbon atoms optionally substituted by alkoxy with 1 to 6 carbon atoms, by hydroxy, by dialkylamino with 1 to 6 carbon atoms in the individual alkyl parts, or by alkoxycarbonyl with up to 6 carbon atoms, $R^2$ represents hydrogen or methyl, Ar represents 2,6-dichloro-4-trifluoromethylphenyl or 2,3,6-trichloro-4-trifluoromethylphenyl, but wherein $R^2$ can represent hydrogen only if $R^1$ does not simultaneously represent methyl.

2. A compound according to claim 1, in which $R^1$ represents methoxyethyl, hydroxyethyl, diethylaminoethyl, methyl, allyl or 1-(ethoxycarbonyl)ethyl.

3. A compound according to claim 1, wherein such compound is 1-(2,6-dichloro-4-trifluoromethyl-phenyl)-5-(2-methoxyethyl-amino)-4-nitro-pyrazole of the formula

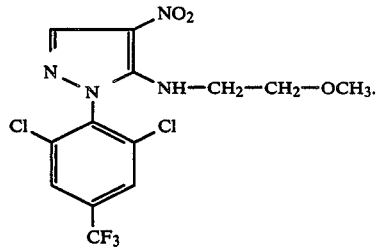

4. A compound according to claim 1, wherein such compuond is 1-(2,6-dichloro-4-trifluoromethyl-phenyl)-5-(2-hydroxyethyl-amino)-4-nitro-pyrazole of the formula

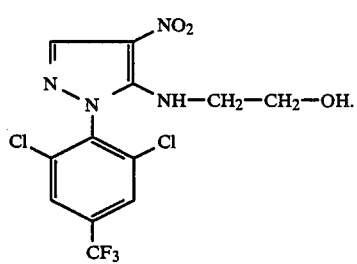

5. A compund according to claim 1, wherein such compound is 1-(2,6-dichloro-4-trifluoromethyl-phenyl)-5-(2-diethylaminoethyl-amino)-4-nitro-pyrazole of the formula

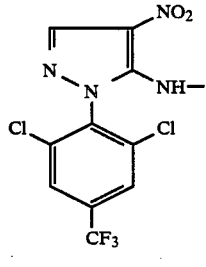

6. A compound according to claim 1, wherein such compound is 1-(2,6-dichloro-4-trifluoromethyl-phenyl)-5-dimethylamino-4-nitro-pyrazole of the formula

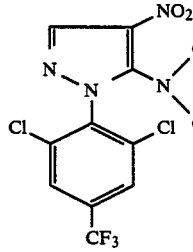

7. A compound according to claim 1, wherein such compound is 1-(2,6-dichloro-4-trifluoromethyl-phenyl)-5-allylamino-4-nitro-pyrazole of the formula

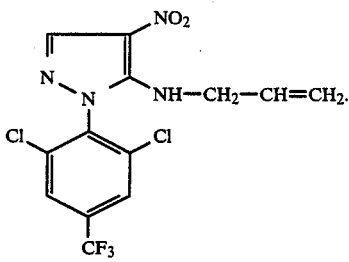

8. A compound according to claim 1, wherein such compound is 1-(2,3,6-trichloro-4-trifluoromethyl-phenyl)-5-allylamino-4-nitro-pyrazole of the formula

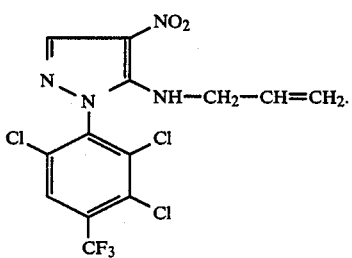

9. A compound according to claim 1, wherein such compound is ethyl α-}N-[1-(2,3,6-trichloro-4-trifluoromethyl-phenyl)-4-nitro-pyrazol-5-yl]-amino}-propionate of the formula

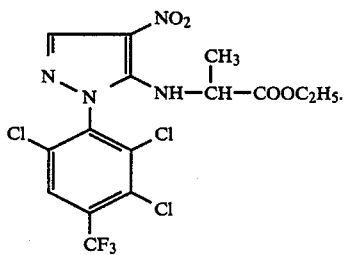

10. A herbicidal or plant growth-regulating composition comprising a herbicidally or plant growth-regulating effective amount of a compound according to claim 1 and a diluent.

11. A method of combating unwanted vegetation which comprises applying to such vegetation or to a locus from which it is desired to exclude such vegetation a herbicidally effective amount of a compound according to claim 1.

12. The method according to claim 11, wherein such compound is
1-(2,6-dichloro-4-trifluoromethyl-phenyl)-5-(2-methoxyethyl-amino)-4-nitro-pyrazole,
1-(2,6-dichloro-4-trifluoromethyl-phenyl)-5-(2-hydroxyethyl-amino)-4-nitro-pyrazole,
1-(2,6-dichloro-4-trifluoromethyl-phenyl)-5-(2-diethylaminoethyl-amino)-4-nitro-pyrazole,
1-(2,6-dichloro-4-trifluoromethyl-phenyl)-5-dimethylamino-4-nitro-pyrazole,
1-(2,6-dichloro-4-trifluoromethyl-phenyl)-5-allylamino-4-nitro-pyrazole,
1-(2,3,6-trichloro-4-trifluoromethyl-phenyl)-5-allylamino-4-nitro-pyrazole or
ethyl α-{N-[1-(2,3,6-trichloro-4-trifluoromethyl-phenyl)-4-nitro-pyrazol-5-yl]-amino}propionate.

13. A method of regulating the growth of plants which comprises applying to such plants or to a locus in which such plants are growing or are to be grown a plant growth-regulating effective amount of a compound according to claim 1.

14. The method according to claim 13, wherein such compound is
1-(2,6-dichloro-4-trifluoromethyl-phenyl)-5-(2-methoxyethyl-amino)-4-nitro-pyrazole,
1-(2,6-dichloro-4-trifluoromethyl-phenyl)-5-(2-hydroxyethyl-amino)-4-nitro-pyrazole,
1-(2,6-dichloro-4-trifluoromethyl-phenyl)-5-(2-diethylaminoethyl-amino)-4-nitro-pyrazole,
1-(2,6-dichloro-4-trifluoromethyl-phenyl)-5-dimethylamino-4-nitro-pyrazole,
1-(2,6-dichloro-4-trifluoromethyl-phenyl)-5-allylamino-4-nitro-pyrazole,
1-(2,3,6-trichloro-4-trifluoromethyl-phenyl)-5-allylamino-4-nitro-pyrazole or
ethyl α-{N-[1-(2,3,6-trichloro-4-trifluoromethyl-phenyl)-4-nitro-pyrazol-5-yl]-amino}propionate.

* * * * *